United States Patent [19]

Tsubouchi et al.

[11] Patent Number: 4,703,124
[45] Date of Patent: Oct. 27, 1987

[54] PROCESS FOR INTRODUCTION OF STYRENES IN SIDE CHAIN OF SUBSTITUTED AROMATIC COMPOUNDS

[75] Inventors: Toshiyuki Tsubouchi; Tomiyasu Minokami; Nobuaki Shimizu, all of Sodegaura, Japan

[73] Assignee: Idemitsu Kosan Company Limited, Tokyo, Japan

[21] Appl. No.: 810,933

[22] Filed: Dec. 19, 1985

[30] Foreign Application Priority Data

Dec. 28, 1984 [JP] Japan ................................. 274576

[51] Int. Cl.$^4$ .................. C07D 213/127; C07C 15/46
[52] U.S. Cl. ................................... 546/352; 585/435; 585/436; 585/437
[58] Field of Search ................ 546/352; 585/24, 26, 585/27, 435, 436, 437

[56] References Cited

FOREIGN PATENT DOCUMENTS 850114  1/1959  European Pat. Off. ............ 546/352

*Primary Examiner*—Richard A. Schwartz
*Assistant Examiner*—J. Richter
*Attorney, Agent, or Firm*—Frishauf, Holtz, Goodman & Woodward

[57] ABSTRACT

A process for introduction of styrenes in the side chain of substituted aromatic compounds, said side chain containing at least one hydrogen atom in the α-position thereof, is disclosed, comprising reacting the styrenes and the substituted aromatic compounds in the presence of (A) an alkali metal and (B) a compound containing a benzyloxy group or alkyl and/or aryl-substituted benzyloxy group. Use of (A) and (B) as a reaction accelerator permits to introduce the styrenes in the side chain of the substituted aromatic compounds in high yield and selectivity.

20 Claims, No Drawings

PROCESS FOR INTRODUCTION OF STYRENES IN SIDE CHAIN OF SUBSTITUTED AROMATIC COMPOUNDS

BACKGROUND OF THE INVENTION

The present invention relates to a process for introduction of styrenes in the side chain of substituted aromatic compounds. More particularly, it is concerned with a process for introducing styrenes in the side chain of substituted aromatic compounds with high efficiency in the presence of a specific accelerator.

For introduction of styrenes in the side chain of substituted aromatic compounds, more specifically compounds having at least one hydrogen atom in the $\alpha$-position of the side chain, such as cumene, ethylbenzene, and toluene, a method using metallic sodium and sodium isopropoxide has been known.

The above method, however, fails to introduce syrenes in the side chain of substituted aromatic compounds with satisfactory results. Particularly in the reaction of cumene and styrene, the selectivity of the desired product (as determined based on styrene) is as low as 15%.

It has therefore been desired to develop a method whereby styrenes can be introduced in the side chain of substituted aromatic compounds with high conversion and high selectivity.

SUMMARY OF THE INVENTION

The major object of the present invention is to provide a process which permits the introduction of styrenes in the side chain, i.e., substituent of substituted aromatic compounds with high efficiency.

It has been found that the object can be attained by reacting styrenes and substituted aromatic compounds in the presence of alkali metals and compounds containing a benzyloxy group or an alkyl and/or aryl-substituted benzyloxy group.

Accordingly the present invention relates to a process for introducing styrenes in the side chain of substituted aromatic compounds, said side chain containing at least one hydrogen atom in the $\alpha$-position thereof, which comprises reacting the styrenes and the substituted aromatic compounds in the presence of (A) an alkali metal and (B) a compound containing a benzyloxy group or an alkyl and/or aryl-substituted benzyloxy group.

DETAILED DESCRIPTION OF THE INVENTION

Substituted aromatic compounds which are used as the starting material in the present invention must contain at least one hydrogen atom linked to a carbon atom in the $\alpha$-position or $\alpha$-positioned carbon atom of the side chain. That is, in the reaction of the present invention, the $\beta$-positioned carbon atom of the styrenes is linked to the $\alpha$-positioned carbon atom of the side chain of the substituted aromatic compounds, resulting in saturation of the $\alpha,\beta$-double bond of the styrenes and, therefore, the desired reaction does not proceed satisfactorily unless one or more hydrogen atoms are bound to the $\alpha$-positioned carbon atom of the side chain of the substituted aromatic compounds.

The side chain or substituent of the substituted aromatic compounds is usually a hydrocarbon group having 1 to 14 carbon atoms. Typical examples of such hydrocarbon groups are alkyl groups such as a methyl group, an ethyl group, a normal-propyl group, an iso-propyl group, a normal-butyl group, an iso-butyl group, and a secondary-butyl group. In addition, cycloalkyl groups such as a cyclohexyl group, and aralkyl groups are included. It is not always necessary for the substituted aromatic compounds of the present invention to be substituted with a single side chain, but they may be substituted with one or more side chains. The substituted aromatic compounds of the present invention also include those compounds in which two side chains are combined together to form a ring, such as indane.

The aromatic ring of the substituted aromatic compounds of the present invention includes a benzene ring, a naphthalene ring, and a pyridine ring.

Typical examples of the substituted aromatic compounds of the present invention are toluene, 1-methylnaphthalene, 2-methylnaphthalene, ortho-xylene, meta-xylene, para-xylene, pseudocumene, 2-methylbiphenyl, 3-methylbiphenyl, 2-methylpyridine, 3-methylpyridine, 4-methylpyridine, 4-methylpyridine, ethylbenzene, normal-propylbenzene, 1-ethylnaphthalene, 2-ethylnaphthalene, indane, tetralin, ethyldiphenyl, fluorene, 2-ethylpyridine, 3-ethylpyridine, 4-ethylpyridine, cumene, secondary-butylbenzene, diisopropylbenzene, 1-isopropylnaphthalene, 2-isopropylnaphthalene, and cyclohexylbenzene.

Styrenes which are introduced in the side chain of the substituted aromatic compounds include, as well as styrene, nucleus-substituted styrenes such as para-methylstyrene and ortho-methylstyrene, and side chain-substituted sytrenes such as $\alpha$-methylstyrene and $\beta$-methylstyrene.

In accordance with the process of the present invention, the above substituted aromatic compounds and styrenes are reacted in the presence of (A) an alkali metal and (B) a compound having a benzyloxy group or alkyl and/or arylsubstituted benzyloxy group. As the alkali metal (A), lithium, sodium, potassium and the like are used. Usually sodium is preferred.

The compound (B) having a benzyloxy group or alkyl and/or aryl-substituted benzyloxy group includes those compounds capable of existing in the reaction system as an ion represented by the general formula:

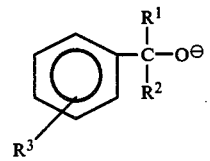

wherein $R^1$, $R^2$ and $R^3$ are each a hydrogen atom, an alkyl group having 1 to 3 carbon atoms, or an aryl group, and $R^2$ and $R^3$ may be linked to each other.

Typical examples of the compound (B) are benzyl alcohol, cumyl alcohol, $\alpha$-phenetyl alcohol, dicumyl peroxide, $\alpha$-phenetyl peroxide, cumene hydroperoxide, and tetralin hydroperoxide.

The ratio of the styrenes to the substituted aromatic compounds varies depending on the desired product, reaction conditions and so forth. For example, in a case where one styrene compound is intended to be introduced in the side chain of the substituted aromatic compounds, the molar ratio of the substituted aromatic compound to the styrene compound is 10:1 to 1:1.5 and preferably 5:1 to 1:1. In a case where a plurality (two or more) of styrenes are intended to be introduced in the side chain, the above molar ratio is adjusted depending on the number of styrenes to be introduced.

Although in the present invention a predetermined amount of styrenes may be added to the substituted aromatic compounds at one time, it is preferred that the styrenes be gradually added while heating in the presence of the alkali metal (A) and the compound (B).

The amount of the alkali metal (A) used is determined appropriately depending on various conditions. Usually the molar ratio of the alkali metal (A) to the compound (B) is 1:100 to 1:2, with the range of 1:50 to 1:5 being preferred. If the amount of the alkali metal (A) used is too small, the yield and selectivity of the desired product are undesirably low. On the other hand, if the amount of the alkali metal (A) used is too large, a large amount of the alkali metal (A) remains after completion of the reaction and, therefore, additional complicated operations such as recovery and decomposition are needed.

The amount of the compound (B) used is also not critical. In general, the molar ratio of the compound (B) to the alkali metal (A) is 1:50 to 1:1 and preferably 1:5 to 1:1.

In the process of the present invention, the reaction temperature, pressure, reaction time, and so forth are not critical and can be determined appropriately. The reaction temperature, for example, is usually 80° to 250° C. and preferably more higher than the melting point of the alkali metal (A). The reaction pressure is usually atmospheric pressure and if a low boiling compound is used as the starting material, the reaction is carried out under pressure if necessary. The reaction time is usually 5 minutes to 3 hours after the addition of the styrenes is completed.

Although in the process of the present invention the total amount of the styrenes may be added at one time to the substituted aromatic compounds previously placed in the reaction system, it is preferred that the styrenes be added dropwise gradually after heating. In this case, if necessary, the styrenes may be diluted with the above substituted aromatic compounds and other hydrocarbons, for example.

After completion of the reaction, the alkali metal is removed from the reaction system by physical or chemical techniques such as filtration and decomposition with alcohols. The resulting oily layer is then separated and purified, whereupon various compounds derived by introduction of the styrenes in the side chain of the substituted aromatic compounds can be obtained in high purity and yield.

In accordance with the process of the present invention, as described above, the introduction of styrenes is carried out in the presence as a reaction accelerator of (A) an alkali metal and (B) a compound containing a benzyloxy group or alkyl and/or aryl-substituted benzyloxy group and, therefore, the desired compounds can be obtained in high yield and selectivity as compared with the conventional methods.

In the process of the present invention, various types of compounds can be produced by changing the type of the starting material, the amount of the starting material used, and so forth. These compounds can be used as, for example, high boiling solvents, traction drive fluids, and further as intermediates for use in chemical industry.

The present invention is described in greater detail with reference to the following examples.

EXAMPLE 1

A one-liter glass flask equipped with a stirrer, a dropping funnel with a gas introduction conduit, a reflux condenser with a calcium chloride tube, and a thermometer was charged with 240 grams (2.0 moles) of purified cumene, 4.0 grams (0.17 mole) of metallic sodium, and 3.6 grams (0.02 mole) of 80% cumene hydroperoxide while introducing argon gas through the gas introduction conduit, and the resulting mixture was heated to 135° C. A mixture of 69 grams (0.66 mole) of purified styrene and 60 grams (0.50 mole) of purified cumene was dropped thereto with stirring over 2 hours while maintaining the temperature of the reaction system at 135°–140° C. After dropwise addition was completed, the reaction mixture was further stirred while heating for 1 hour and then cooled to room temperature. An excess of metallic sodium was decomposed by dropping methanol in small portions while stirring. Introduction of argon gas was stopped, and the contents were transferred to a separating funnel and washed with water. The aqueous layer was removed, and the remaining oily layer was analyzed by gas chromatography. This gas chromatographic analysis showed that 67.6 grams (0.31 mole) of 1,3-diphenyl-3-methylbutane and 36.5 grams of (0.11 mole) of 1,3,5-triphenyl-5-methylhexane were formed. The total yield (per styrene) was 80 mole %.

COMPARATIVE EXAMPLE 1

The procedure of Example 1 was repeated wherein 1.2 grams (0.02 mole) of isopropyl alcohol was used in place of cumene hydroperoxide. Then 3.8 grams (0.017 mole) of 1,3-diphenyl-3-methylbutane and 7.0 grams (0.021 mole) of 1,3,5-triphenyl-5-methylhexane were formed. The total yield (per styrene) was 8.9 mole %.

COMPARATIVE EXAMPLE 2

The procedure of Example 1 was repeated wherein 2.53 grams (0.02 mole) of orthochlorotoluene was used in place of cumene hydroperoxide. Then 11.8 grams (0.052 mole) of 1,3-diphenyl-3-methylbutane and 7.7 grams (0.024 mole) of 1,3,5-triphenyl-5-methylhexane were formed. The total yield (per styrene) was 15 mole %.

EXAMPLE 2

The procedure of Example 1 was repeated wherein 2.7 grams (0.02 mole) of cumyl alcohol was used in place of cumene hydroperoxide. Then 64.0 grams (0.29 mole) of 1,3-diphenyl-3-methylbutane and 32.3 grams (0.10 mole) of 1,3,5-triphenyl-5-methylhexane were formed. The total yield (per styrene) was 74 mole %.

EXAMPLE 3

The procedure of Example 1 was repeated wherein 2.4 grams (0.02 mole) of α-phenethyl alcohol was used in place of cumene hydroperoxide. Then 77.7 grams (0.34 mole) of 1,3-diphenyl-3-methylbutane and 35.7 grams (0.11 mole) of 1,3,5-triphenyl-5-methylhexane were formed. The total yield (per styrene) was 85 mole %.

EXAMPLE 4

The procedure of Example 1 was repeated wherein 2.2 grams (0.02 mole) of benzyl alcohol was used in place of cumene hydroperoxide. Then 33.2 grams (0.15 mole) of 1,3-diphenyl-3-methylbutane and 30.1 grams (0.09 mole) of 1,3,5-triphenyl-5-methylhexane were formed. The total yield (per styrene) was 50 mole %.

EXAMPLE 5

The procedure of Example 1 was repeated wherein 5.4 grams (0.02 mole) of dicumyl peroxide was used in place of cumene hydroperoxide. Then 60.8 grams (0.27 mole) of 1,3-diphenyl-3-methylbutane and 31.0 grams (0.09 mole) of 1,3,5-methylhexane were formed. The total yield (per styrene) was 69 mole %.

EXAMPLE 6

A one-liter glass flask equipped with a stirrer, a dropping funnel with a gas introduction conduit, a reflux condenser with a calcium chloride tube, and a thermometer was charged with 212 grams (2.0 moles) of purified ethylbenzene, 4.0 grams (0.17 mole) of metallic sodium, and 2.9 grams (0.02 mole) of cumene hydroperoxide while introducing argon gas through the gas introduction conduit, and the resulting mixture was heated to 135° C. Then 208 grams (2.0 moles) of purified styrene were added dropwise thereto with stirring over 2 hours while maintaining the temperature of the reaction system at 135° C. After dropwise addition was completed, the reaction mixture was further stirred while heating for 1 hour and then cooled to room temperature. An excess of metallic sodium was decomposed by dropping methanol in small portions while stirring. Introduction of argon gas was stopped, and the contents were transferred to a separating funnel and then washed with water. The aqueous layer was removed, and the remaining oily layer was analyzed by gas chromatograpy. This gas chromatographic analysis showed that 96.6 grams (0.94 mole) of 1,3-diphenylbutane was formed. The yield was 47 mole %.

EXAMPLE 7

A one-liter glass flask equipped with a stirrer, a dropping funnel with a gas introduction conduit, a reflux condenser with a calcium chloride tube, and a thermometer was charged with 268 grams (2.0 moles) of purified secondary butylbenzene, 4.0 grams (0.17 mole) of metallic sodium and 2.4 grams (0.02 moles) of α-phenethyl alcohol while introducing argon gas through the gas introduction conduit, and the resulting mixture was heated to 135° C. Then 69 grams (0.66 mole) of purified styrene and 20 grams (0.15 mole) of secondary butylbenzene were dropped thereto over 2 hours while maintaining the temperature of the reaction system at 135° C. After dropwise addition was completed, the reaction mixture was stirred while heating for 1 hour and then cooled to room temperature. An excess of metallic sodium was decomposed by dropping methanol in small portions while stirring. Introduction of argon gas was stopped, and the contents were transferred to a separating funnel and then washed with water. The aqueous laer was removed, and the remaining oily layer was analyzed by gas chromatography. This gas chromatographic analysis showed that 40.7 grams (0.17 mole) of 1,3-dipenyl-3-methylpentane and 31.4 grams (0.092 mole) of 1,3,5-triphenyl-5-methylpentane were formed. The total yield (per styrene) was 54 mole %.

EXAMPLE 8

A one-liter glass flask equipped with a stirrer, a dropping funnel with a gas introduction conduit, a reflux with a calcium chloride tube, and a thermometer was charged with 240 grams (2.0 moles) of commercially available cumene saturated with water, 4.0 grams (0.17 mole) of metallic sodium, and 2.7 grams (0.02 mole) of cumyl alcohol while introducing argon gas through the gas introduction conduit, and the resulting mixture was heated to 135° C. A mixture of 69 grams (0.66 mole) of commercially available styrene saturated with water and 60 grams (0.50 mole) of commercially available cumene saturated with water was dropped thereto over 2 hours with stirring while maintaining the temperature of the reaction system at 135°–140° C. After dropwise addition was completed, the reaction mixture was further stirred while heating for 1 hour and then cooled to room temperature. An excess of metallic sodium was decomposed by dropping methanol in small portions while stirring. Introduction of argon gas was stopped, and the contents were transferred to a separating funnel and then washed with water. The aqueous layer was removed, and the remaining oily layer was analyzed by gas chromatography. This gas chromatographic analysis showed that 58.7 grams (0.26 mole) of 1,3-diphenyl-3-methylbutane and 36.9 grams (0.11 mole) of 1,3,5-triphenyl-5-methylhexane were formed. The total yield (per styrene) was 73 mole %.

COMPARATIVE EXAMPLE 3

The procedure of Example 8 was repeated wherein 1.2 grams (0.02 mole) of isopropyl alcohol was used in place of cumyl alcohol. The total yield (per styrene) of the 1,3-diphenyl-3-methylbutane and 1,3,5-triphenyl-5-methylhexane formed was less than 3 mole %.

What is claimed is:

1. A process for introducing one or two styrenes into a first hydrocarbon side chain of a substituted aromatic compound wherein the substituents are one or more hydrocarbon side chains having 1 to 14 carbon atoms, said first hydrocarbon side chain being one of said substituents having 1 to 14 carbon atoms and having at least one hydrogen atom in the α-position thereof, said process comprising reacting the styrene and the substituted aromatic compound in the presence of (A) an alkali metal and (B) a compound containing a benzyloxy group, an alkyl-substituted benzyloxy group, an aryl-substituted benzyloxy group, or an alkyl and aryl-substituted benzyloxy group.

2. The process as claimed in claim 1, wherein said substituted aromatic compound is a derivative of benzene, naphthalene, or pyridine.

3. The process as claimed in claim 1, wherein the substituted aromatic compound having a side chain containing at least one hydrogen atom in the α-position thereof is toluene, 1-methylnaphthalene, 2-metylnaphthalene, o-xylene, m-xylene, p-xylene, pseudocumene, 2-methylbiphenyl, 3-methylbiphenyl, 2-methylpyridine, 3-methylpyridine, 4-methylpyridine, ethylbenzene, n-propylbenzene, 1-ethylnaphtha-lene, 2-ethylnaphthalene, indane, tetralin, ethyldiphenyl, fluorene, 2-ethylpyridine, 3-ethylpyridine, 4-ethylpyridine, cumene, secondary butylbenzene, diisopropylbenzene, 1-isopropylnaphthalene, 2-isopropylnaphthalene or cyclohexylbenzene.

4. The process as claimed in claim 1, wherein said compound (B) is benzyl alcohol, cumyl alcohol, α-phenethyl alcohol, cumyl peroxide, dicumyl peroxide, α-phenethyl peroxide, cumene hydroperoxide or tetralin hydroperoxide.

5. The process as claimed in claim 1, wherein said compound (B) is a compound capable of existing in the reaction system as an ion having the formula:

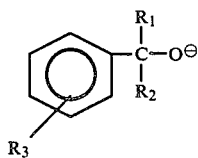

wherein $R_1$, $R_2$ and $R_3$ are each hydrogen, $C_{1-3}$ alkyl or aryl and wherein $R_2$ and $R_3$ may be joined together.

6. The process as claimed in claim 1, wherein one styrene is to be introduced into said first side chain of said substituted aromatic compound, and the molar ratio of said substituted aromatic coumpound to the styrene compound is 10:1 to 1:1.5.

7. The process as claimed in claim 1, wherein said alkali metal (A) is lithium, sodium or potassium.

8. The process as claimed in claim 1, wherein the molar ratio of said alkali metal (A) to said compound (B) is 1:100 to 1:2.

9. The process as claimed in claim 1, wherein said reaction is carried out at a temperature of from 80° to 250° C.

10. The process as claimed in claim 1, wherein said styrene reactant is styrene, paramethylstyrene, orthomethylstyrene, α-methylstyrene or β-methylstyrene.

11. The process as claimed in claim 10, wherein said substituted aromatic compound is cumene, said (A) is sodium and said compound (B) is cumene hydroperoxide.

12. The process as claimed in claim 10, wherein said substituted aromatic compound is cumene, said (A) is sodium and said compound (B) is cumyl alcohol.

13. The process as claimed in claim 1, wherein said substituted aromatic compound is cumene, said (A) is sodium and said compound (B) is a α-phenethyl alcohol.

14. The process as claimed in claim 1, wherein said substituted aromatic compound is cumene, said (A) is sodium and said compound (B) is benzyl alcohol.

15. The process as claimed in claim 1, wherein said substituted aromatic compound is cumene, said (A) is sodium and said compound (B) is dicumyl hydroperoxide.

16. The process as claimed in claim 1, wherein said substituted aromatic compound is ethylbenzene, said (A) is sodium and said compound (B) is cumene hydroperoxide.

17. The process as claimed in claim 1, wherein said substituted aromatic compound is secondary butylbenzene, said (A) is sodium and said compound (B) is α-phenethyl alcohol.

18. The process as claimed in claim 3, wherein said styrene reactant is styrene, paramethylstyrene, orthomethylstyrene, α-methylstyrene or β-methylstyrene.

19. The process as claimed in claim 18, wherein said alkali metal (A) is lithium, sodium or potassium.

20. The process as claimed in claim 19, wherein one styrene is to be introduced into said first side chain of said substituted aromatic compound, and the molar ratio of said substituted aromatic compound to the styrene compound is 10:1 to 1:1.5 and said reaction is carried out at a temperature of from 80° to 250° C.

* * * * *